(12) United States Patent
Allinniemi et al.

(10) Patent No.: US 9,078,714 B2
(45) Date of Patent: Jul. 14, 2015

(54) BONE FIXATION DEVICE

(75) Inventors: Timo Allinniemi, Lempäälä (FI); Harri Heino, Tampere (FI); Pertti Törmälä, Tampere (FI)

(73) Assignee: BIORETEC OY, Tampere (FI)

( * ) Notice: Subject to any disclaimer, the term of this patent is extended or adjusted under 35 U.S.C. 154(b) by 1601 days.

(21) Appl. No.: 11/808,074

(22) Filed: Jun. 6, 2007

(65) Prior Publication Data
US 2007/0299449 A1 Dec. 27, 2007

(30) Foreign Application Priority Data
Jun. 6, 2006 (FI) ..................... 20065385

(51) Int. Cl.
| A61B 17/58 | (2006.01) |
| A61B 17/84 | (2006.01) |
| A61B 17/86 | (2006.01) |
| A61B 17/04 | (2006.01) |
| A61B 17/68 | (2006.01) |
(Continued)

(52) U.S. Cl.
CPC ........... *A61B 17/846* (2013.01); *A61B 17/0401* (2013.01); *A61B 17/68* (2013.01); *A61B 17/84* (2013.01); *A61B 17/86* (2013.01); *A61B 17/8625* (2013.01); *A61B 17/92* (2013.01); *A61L 31/148* (2013.01); *A61B 17/863* (2013.01); *A61B 17/864* (2013.01); *A61B 17/865* (2013.01); *A61B 17/8645* (2013.01); *A61B 2017/00004* (2013.01); *A61B 2017/00858* (2013.01); *A61B 2017/00898* (2013.01); *A61B 2017/8655* (2013.01)

(58) Field of Classification Search
CPC ...... A61B 17/84; A61B 17/846; A61B 17/86; A61B 2017/8655; A61B 17/68; A61B 17/8625; A61B 17/863; A61B 17/864; A61B 17/8645; A61B 2017/00004; A61B 2017/00858; A61L 31/148
USPC ......... 606/232, 250–256, 258–262, 264–275, 606/278–279, 86 R, 246, 300–331, 908, 606/62–63
See application file for complete search history.

(56) References Cited

U.S. PATENT DOCUMENTS 4,532,926 A * 8/1985 O'Holla ..................... 606/220
4,671,280 A 6/1987 Dorband et al.
(Continued)

FOREIGN PATENT DOCUMENTS

DE 3919900 A1 12/1990
EP 0321176 A2 6/1989
(Continued)

OTHER PUBLICATIONS

European Search Report—Nov. 7, 2007.

*Primary Examiner* — Larry E Waggle, Jr.
(74) *Attorney, Agent, or Firm* — Venable LLP; Eric J. Franklin

(57) ABSTRACT

The present invention relates to a bioabsorbable osteosynthesis fixation device for the fixation of bone fractures or osteotomies. The fixation device comprises a tip, a shaft and a head. The periphery of the shaft comprises ridges which extend in a direction which forms an angle with the longitudinal axis of the shaft, the angle being between −45° and 45°. The present invention also relates to a method for manufacturing the bioabsorbable osteosynthesis fixation device.

23 Claims, 14 Drawing Sheets

(51) Int. Cl.
*A61B 17/92* (2006.01)
*A61L 31/14* (2006.01)
*A61B 17/00* (2006.01)

(56) References Cited

U.S. PATENT DOCUMENTS

| | | | |
|---|---|---|---|
| 4,898,186 A | | 2/1990 | Ikada et al. |
| 4,968,317 A | * | 11/1990 | Tormala et al. ............ 606/77 |
| 5,053,035 A | * | 10/1991 | McLaren .................. 606/67 |
| 5,094,618 A | * | 3/1992 | Sullivan .................... 433/173 |
| 5,246,441 A | * | 9/1993 | Ross et al. ................. 606/53 |
| 5,275,601 A | | 1/1994 | Gogolewski et al. |
| 5,562,704 A | | 10/1996 | Tamminmäki et al. |
| 5,618,286 A | * | 4/1997 | Brinker .................... 606/60 |
| 6,015,410 A | | 1/2000 | Törmälä et al. |
| 6,096,060 A | * | 8/2000 | Fitts et al. ................. 606/232 |
| 6,162,253 A | | 12/2000 | Conzemius et al. |
| 6,221,075 B1 | | 4/2001 | Tormala et al. |
| 6,296,641 B2 | | 10/2001 | Burkhead et al. |
| 6,503,278 B1 | | 1/2003 | Pohjonen et al. |
| 6,551,343 B1 | * | 4/2003 | Tormala et al. ............ 606/213 |
| 6,723,099 B1 | | 4/2004 | Goshert |
| 2002/0143340 A1 | | 10/2002 | Kaneko |
| 2002/0177851 A1 | * | 11/2002 | Happonen et al. ........ 606/73 |
| 2003/0014127 A1 | * | 1/2003 | Talja et al. ................ 623/23.75 |
| 2003/0083745 A1 | | 5/2003 | Pohjonen et al. |
| 2003/0088252 A1 | * | 5/2003 | Kaikkonen et al. ....... 606/76 |
| 2004/0097945 A1 | * | 5/2004 | Wolf ........................ 606/73 |
| 2005/0123581 A1 | | 6/2005 | Ringeisen et al. |
| 2005/0187555 A1 | * | 8/2005 | Biedermann et al. ..... 606/72 |

FOREIGN PATENT DOCUMENTS

| | | | | |
|---|---|---|---|---|
| EP | 336100 A2 | * | 10/1989 | ......... A61B 17/58 |
| EP | 0 336 100 B1 | | 9/1993 | |
| WO | WO-88/05312 A1 | | 7/1988 | |
| WO | WO-98/51241 A1 | | 11/1998 | |
| WO | WO 9851241 A1 | * | 11/1998 | |
| WO | WO-99/51159 A1 | | 10/1999 | |

* cited by examiner

BONE FIXATION DEVICE

FIELD OF THE INVENTION

The present invention relates to a bioabsorbable osteosynthesis fixation device, such as a pin or a tack.

More precisely, the invention relates to an osteosynthesis fixation device made of a bio-compatible material which is entirely absorbable in vivo. The fixation device is in a form of an elongated object. It exhibits sufficient mechanical properties to provide efficacious and reliable support to, for example, a traumatized skeleton, for a sufficiently long period of time to allow for consolidation and repair of bone fractures and/or osteotomies. It also exhibits good bioabsorbability, sufficient to avoid a second surgical intervention, such as is frequently required to remove metallic osteosynthesis devices.

BACKGROUND OF THE INVENTION

In surgery, it is known to employ implants manufactured of biodegradable (under tissue conditions absorbable) polymers for connecting tissues together, and for securing the healing or growth of the tissues. It is known to manufacture of partly crystalline or amorphous thermoplastic, biodegradable polymers strong implant materials by stretching elongated blanks, such as bars, in a such manner that the structure of the materials is modified and directed (oriented) increasing the strength and the stiffness of the material in the direction of orientation.

U.S. Pat. No. 4,671,280 describes a tissue fastening device comprising (a) a fastener member having a pair of legs extending from the same side of a connecting cross piece, said fastener member adapted to be placed on one side of the tissue to be joined with the legs penetrating the tissues, said fastener member being an oriented crystalline polymeric material, whereby the fastener member has sufficient inherent strength and stiffness so that said legs can penetrate the tissue to be fastened, and (b) a receiver member to secure said fastener member in place. U.S. Pat. No. 4,671,280 describes the method to increase strength and stiffness of a tissue fastening device with solid state orientation (drawing the fastening device preform to the draw ratio of ca. 7 X).

U.S. Pat. No. 4,898,186 describes an osteosynthetic pin characterized in that the pin is formed substantially of a poly-L-lactic acid having a molecular weight of approximately at least 70,000, and is formed by axially drawing ca 2 to ca 10 times at an elevated temperature of ca 70° to ca 120° C. The osteosynthetic pin of U.S. Pat. No. 4,898,186 can be of any desired shape, for example, in the form of a plate, polygonal prism (such as quadrangular, pentagonal, hexagonal or octagonal prism), solid cylinder or the like. Polygonal prism structure may give for the pin a moderate rotational stability, but it needs an exact diameter of the drillhole in the bone, because polygonal prism structure cannot deform significantly if the drillhole is a bit too small in relation to the maximum transverse diameter of the pin.

U.S. Pat. No. 4,968,317 describes a surgical composite comprising a material selected from the group of resorbable polymer, resorbable copolymer, and mixtures thereof and further containing oriented, at least partially fibrillated structural units (fibrils) which have been induced into the material providing said units while said material is in its original nonfibrillar state by drawing said material in solid state. This patent describes also rods made of fibrillated material.

At higher drawing ratios (typically at drawing ratios of 7 to 10 or higher) (partial) fibrillation or self-reinforcing of material takes place, as is described in U.S. Pat. No. 4,968,317. (Partially) fibrillated materials have good strength properties in the direction of drawing, but these materials have poor strength properties in the direction perpendicular to the drawing direction, because longitudinal fibrils easily separate from each other. Therefore peeling of fibrous material from the surface of a pin, tack or mechanically machined screw may occur easily when a fibrillated (self-reinforced) pin, tack or screw is inserted into a drillhole in a bone.

U.S. Pat. No. 6,503,278 describes a material that degrades after implantation into patient's tissue, and resorbs into the patient's body, which material is manufactured of polymer, copolymer or polymer alloy. The material has a non-crystalline, i.e. amorphous structure and is molecularly oriented and reinforced by mechanical deformation. Further, the material can be formed into surgical devices, such as screws and pins, for implantation into a patient.

Pin with a solid cylinder structure needs a drillhole of specific size, because too large a drillhole gives a loose pin fixation and too small a drillhole prevents totally the insertion of a cylindrical pin. Additionally, the rotational stability of a bone fragment fixed with one smooth, cylindrical pin is poor.

U.S. Pat. No. 6,296,641 describes a substantially bioabsorbable, one-piece implant for tissue fixation comprising: an elongated cannulated shaft having a longitudinal axis and a first end, said first end having first and second sides, said first end comprising a mating surface projecting only from said first side of said elongated cannulated shaft so that said second side of said first end of said elongated cannulated shaft has a smooth surface without a projection, said mating surface being oriented at an angle of less than 90 degrees with respect to said longitudinal axis of said shaft, and said mating surface having a width in a direction perpendicular to the longitudinal axis that is greater than the width of said shaft. A fixation implant generally includes at least one shaft configured to securely fit into a hole formed in bone. The shaft is sufficiently long in relation to the interior diameter of the hole and, in some preferred embodiments, has locking protuberances, such as threads, ridges, or barbs, that resist the removal of the shaft from the hole in the bone when different types of forces, such as tensile or bending forces, are applied to the implant. The locking protuberances of implants of this invention are limited to transverse structures in relation to the longitudinal axis of the implant.

SUMMARY OF THE INVENTION

The invention provides a bone fracture fixation device, such as a pin or a tack, which has a deformable grooved and ridged surface structure and shape so that it can be pushed into a drillhole whose diameter is even smaller than the maximum transverse shaft diameter of the pin or the tack to achieve a good, tight fixation of a bone fragment. The bone fracture fixation device is strong and tough and has a high pull-out load carrying capacity. It also gives good rotational stability for the fixed bone fragment. The fixation device is mainly intended for use in connection with the fractures of the cancellous bones.

The bone fracture fixation device swells in vivo slightly in the direction transverse to its longitudinal axis. The swelling also increases the fixation strength of the fixation device—fixed bone system. The diameter of the fixation device increases at least within first six weeks, preferably at least within first two weeks and most preferably within first 63 hours in a test in vitro.

Further, it can be concluded that the fixation device of the invention promotes the healing process of a bone fracture.

Because the fixation device comprises grooves and ridges on the surface of its shaft, small canals are formed between the bottoms of the grooves and the bony wall surrounding the drillhole. The small canals enhance the circulation of blood and tissue fluids and thus the healing of the fracture takes place more rapidly.

The fixation device may be a part of a kit which in addition to the fixation device comprise a drill comprising a drill bit, or another device for forming a hole. Naturally, the kit can also include more than one fixation device. The kit may also comprise a holder for the/each fixation device, or one holder for a few fixation devices, and an applicator instrument for inserting the fixation device in a hole in a bone.

BRIEF DESCRIPTION OF THE INVENTION

The invention provides a bioabsorbable, sterilizable polymeric or composite bone fracture or osteotomy fixation device, such as a pin comprising a shaft. The surface of the shaft comprises longitudinal grooves. Between the grooves there are naturally ridges. According to the invention, the fixation device can also be a bioabsorbable tack (a pin with an widening head) comprising a shaft. The surface of the shaft is also provided with longitudinal grooves and ridges.

Besides the longitudinal grooves and ridges, the grooves and ridges may form an angle with the longitudinal axis of the fixation device. The angle may be between $-45°$ and $45°$, preferably $-10°$ and $10°$ and more preferably between $-5°$ and $5°$. It is also possible that the grooves and ridges extend spirally around the longitudinal axis of the fixation device.

The pins and tacks with the grooves and ridges on their surface surprisingly have a deformation capacity on their surface so that they can be pushed or tapped into a drillhole in a bone, where the diameter of the drillhole is even smaller than the maximum diameter of the shaft of the pin or tack in the direction perpendicular to the longitudinal axis of the pin or tack. As a consequence, the pin or tack of the invention has a surprisingly good fixation capacity and rotational stability manifested by the high pull-out force from the drillhole and by the high torsion resistance of fixation.

In conventional fixation devices, the maximum diameter of the shaft is generally equal to the nominal diameter of the fixation device. In the fixation device of the invention, the maximum diameter of the shaft of the fixation device exceeds the nominal diameter of the fixation device.

The nominal diameter is a diameter which is given in medical instructions of the fixation device by the manufacturer of the fixation device, and this diameter must be correct because surgeons follow these instructions. The medical instructions are supervised by the FDA in the USA, and they are ruled by directives in Europe.

The osteosynthesis pins and tacks of the present invention can be manufactured of thermoplastic bioabsorbable (bioresorbable or biodegradable) polymers, copolymers, polymer alloys, or composites e.g. of poly-α-hydroxy acids and other aliphatic bioabsorbable polyesters, polyanhydrides, polyorthoesters, polyorganophosphatzenes, tyrosine polycarbonates and other bioabsorbable polymers disclosed in numerous publications, e.g. in S. Vainionpää et al., Prog. Polym. Sci., 14 (1989) 679-716, FI Pat. No. 952884, FI Pat. No. 955547 and WO-90/04982, EP 0449867 B1, U.S. Pat. No. 5,569,250, S. I. Ertel et al., J. Biomed. Mater. Res., 29 (1995) 1337-1348 as well as in the reference publications mentioned in the aforementioned publications.

Pins and tacks in accordance with this invention can be manufactured of bioabsorbable polymers by using one polymer or a polymer alloy. The implants can also be reinforced by reinforcing the material by fibres manufactured of a resorbable polymer or of a polymer alloy, or with biodegradable ceramic fibres, such as β-tricalsiumphosphate fibres, bioactive glass fibres or CaM fibres (cf. e.g. EP146398). Ceramic powders can also be used as additives (fillers) in implants to promote new bone formation.

It is natural that the materials and implants of the invention can also contain various biocompatible additives for facilitating the processability of the material (e.g. stabilizers, antioxidants or plasticizers) or for changing its properties (e.g. plasticizers or ceramic powder materials or biostable fibres, such as carbon) or for facilitating its treatment (e.g. colorants).

According to one advantageous embodiment the implant of the invention contains some other bioactive additive(s), such as antibiotic(s) or other drug(s), chemotherapeutic agents, agents activating healing of wounds, growth factor(s), bone morphogenic protein(s), anticoagulant (such as heparin) etc. Such bioactive implants are particularly advantageous in clinical use, because they have, in addition to their mechanical effect, also biochemical, medical and other effects to facilitate tissue healing and/or regeneration.

The fixation devices of the present invention are typically manufactured in the following way:

First the polymer raw material (+optional additives and/or filler(s) and/or reinforcing fibers) in the form of a powder, flakes, pellets or granulate, etc., will be melted (melt molded) in a continuous process, such as extrusion, or in a discontinuous process, such as injection molding or compression molding. The melted material will be formed to a preform in a mold or die and thereafter it will be cooled so that it solidifies to an amorphous or partially crystalline (crystallinity typically 5-50%) preform, such as a cylindrical rod or bar. Cooling can be accomplished inside a special mold when the injection molding and compression molding techniques are used. In extrusion, the preform will be formed from material melt in a die and the preform will be led onto a special cooling belt or into a cooling solution to produce a solid continuous preform.

The pin or tack of the invention can be formed of the solid preform by processing the grooves and ridges mechanically (e.g. by cutting or milling) on the surface of the pin or tack preform. The tack head can also be formed mechanically (before forming the grooves and ridges) e.g. by milling or by turning on a lathe. The head of a tack can be formed also thermomechanically by compressing or by upsetting the end of a pin.

According to one advantageous embodiment the grooved (and ridged) preform of a pin or tack of the invention is made by molecular orientation in solid state, at a temperature of T>Tg (the glass transition temperature of the material) and T<Tm (the melting temperature, if any, of the material).

A molecular orientation is carried out by modifying biomaterial in solid state mechanically in a temperature where large scale molecular movements are possible, but where thermal movement is not strong enough for the achieved orientation to relax as a result from the molecular thermal movements.

One way of performing the mechanical modification is to draw a melt-processed (such as injection molded, extruded or compression molded), non-oriented billet or preform (such as a rod) to a typical drawing ratio of 2 to 10 in the direction of the longitudinal axis of the billet. Preferably the drawing ratio is between 2 and 5 because when solid state drawing is made with low or medium drawing ratios, the material is oriented in the drawing direction and its strength and modulus increase in the longitudinal direction but no fibrillation occurs. According to this invention the drawing is carried out as a so called die drawing, wherein the billet is drawn through a heated die to a suitable drawing ratio using a die, whose inner surface comprises grooves and ridges, which form the grooved/ridged surface in the billet during drawing. As a result of the drawing, the molecule chains and/or parts thereof are directed increasingly to the draw direction, wherein the strength and toughness of the material increase in the draw direction. It is possible to use ultrasound in the die in order to decrease friction between the die and the bioabsorbable material. Thus, it may be possible to increase the speed of extrusion.

If such ridges and grooves are desired whose angle compared to the longitudinal axis deviates from 0°, it is possible to wind the billet. One end of the billet is engaged to the drawing die and the other is engaged to a pull side. In order to wind the billet it is possible to rotate either the die or the pull side, or both in opposite directions, or both in the same direction with different speeds.

After the drawing, the drawn, grooved and ridged billet is cooled under stress to the room temperature, and implants, such as osteosynthesis pins and tacks can be further processed thereof. Suitable processing methods in this context also include e.g. sawing (cutting), turning on a lathe, milling, shearing and other mechanical processing methods, thermal processing (compression molding under heat and pressure) or combinations of mechanical processing and thermal processing.

When the fixation device is used for fixing a bone fracture, the following method is employed:

A hole is drilled in a bone and a fixation device, e.g. a pin or a tack, is selected according to the dimensions of the hole. The fixation device is packed in a special holder or package which comprises a canal whose diameter corresponds to the largest outer diameter of the fixation device.

The holder can be used in cooperation with a special applicator instrument. The applicator instrument comprises an innermost, piston-like part and an outermost, hollow part which is concentric with the longitudinal axis of the innermost part. The innermost part comprises a tip which is compatible with the cavity or canal of the fixation device. The cavity or canal is concentric with the longitudinal axis of the fixation device. The cavity or the canal of the fixation device can be attached to the tip with a plug connection.

The fixation device is picked from the holder by the innermost part of the applicator instrument by attaching the tip to the cavity or canal of the fixation device. Next, the innermost part with the fixation device is slid inside the outermost part of the applicator instrument.

In the following phase, the outermost part is positioned in the opening of the drillhole and the outermost part is aligned with the longitudinal axis of the drillhole. When the applicator instrument is in a correct position, the fixation device is pushed into the drillhole in the bone by the innermost part, i.e. the innermost part moves inside the outermost part like a piston. The applicator instrument is designed so that the fixation device is embedded half of a millimeter or even a few millimeters below the bone surface when the innermost part is tapped.

BRIEF DESCRIPTION OF THE DRAWINGS

The invention will be described in detail in conjunction with the accompanying drawings wherein:

FIG. 16 shows a magnified view of the cross-section of FIG. 5a.

DETAILED DESCRIPTION OF THE INVENTION

Figure 1A:
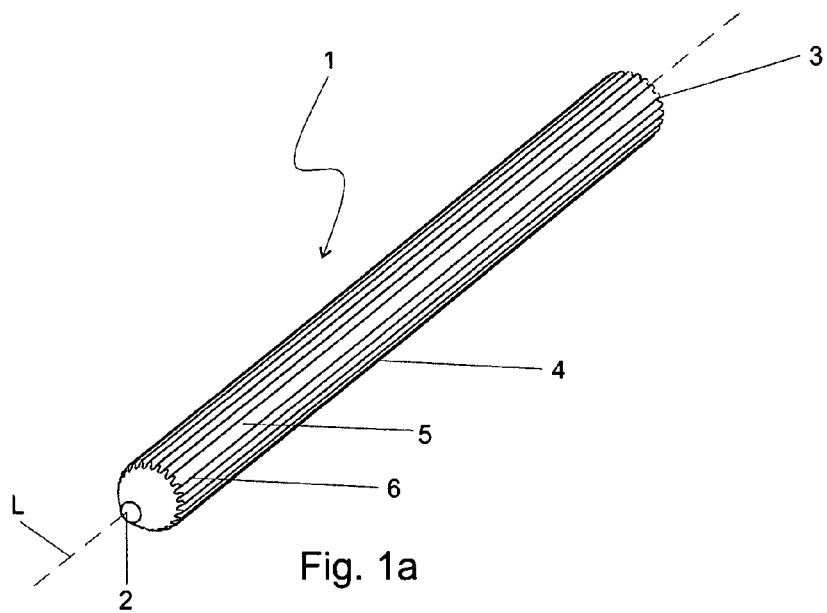
FIGS. 1a-1i show perspective views of pins of the invention.
Figure 1B:
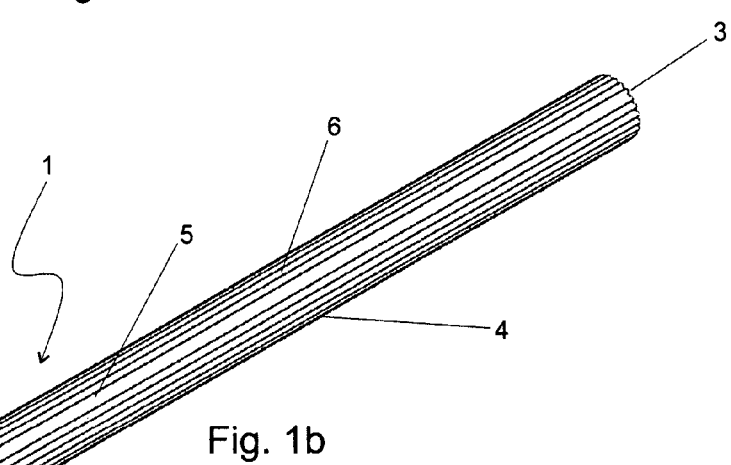

Referring to the drawings, in FIG. 1a there is shown a pin 1 of the invention. The pin 1 comprises a tip 2, a head 3 and a shaft 4, which contains longitudinal grooves 5, which are separated from each other by ridges 6. The grooves 5 and ridges 6 are typically directed in parallel with the longitudinal axis L of the pin 1, but they can also extend spirally around the longitudinal axis L, or they can form an angle with the longitudinal axis L. The tip 2 can be blunt, as shown in FIG. 1b, or sharpened e.g. to a conical or hemispheral form, as shown in FIG. 1a.

Figure 1C:
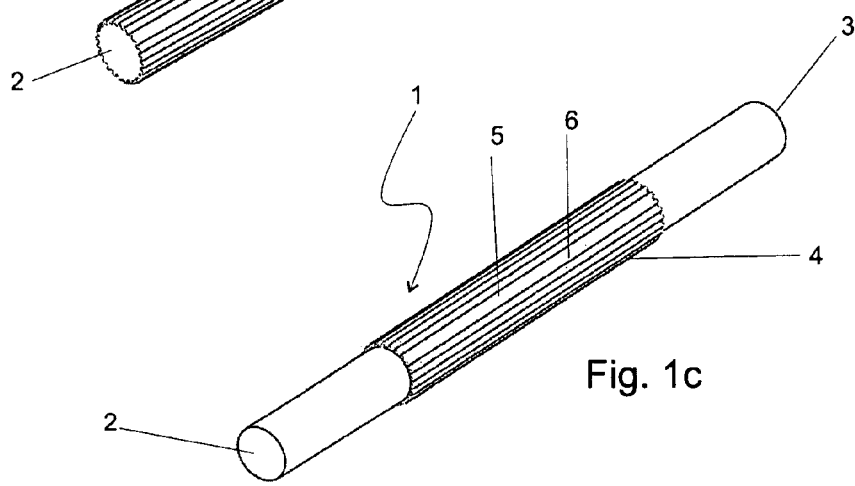

FIG. 1c shows a modification of the pin 1. The ridges 6 and grooves 5 cover only partially the surface of the shaft 4 in such a manner that only the central part of the shaft 4 is covered with the ridges 6 and grooves 5.

Figure 1D:
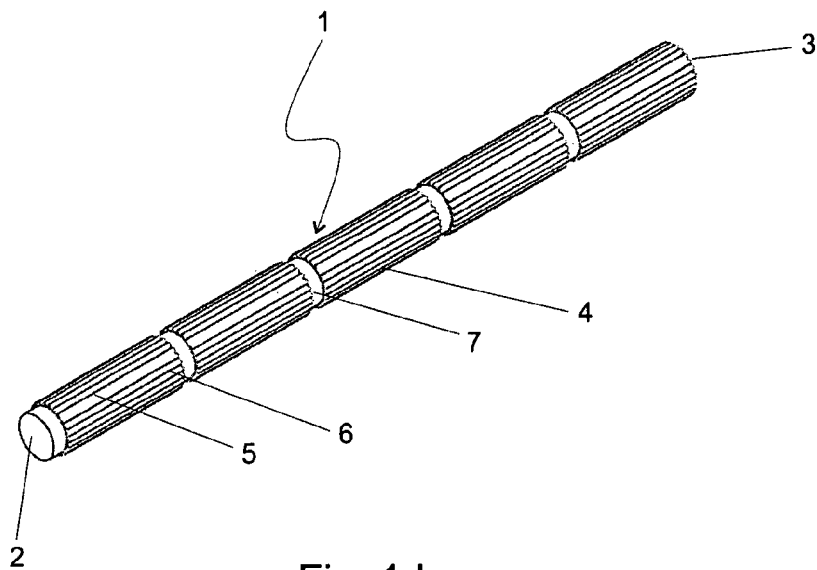

FIG. 1d shows a pin 1 whose ridges 6 and grooves 5 are discontinuous. An annular space 7 separates the groups of the ridges 6 and grooves 5 from each other.

Figure 1E:
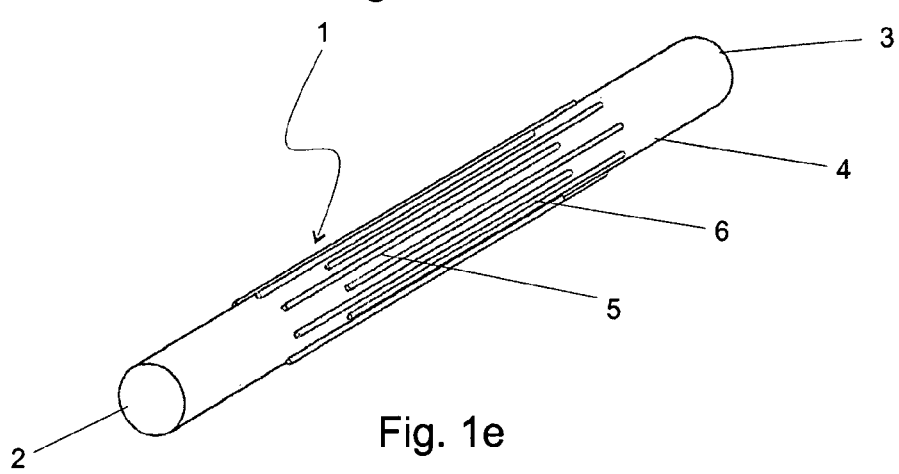

FIG. 1e shows a pin 1 which also has ridges 6 and grooves 6 in the central part of the pin as in FIG. 1c, but the ridges 6 have alternating starting points. The ridges 6 may differ in length.

Figure 1F:
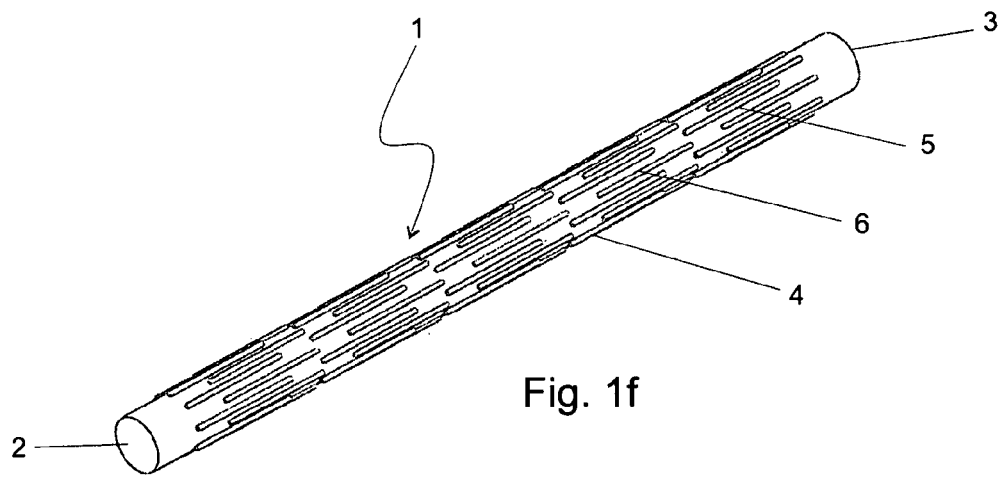

FIG. 1f shows a pin 1 which is a hybrid of the pins of FIGS. 1d and 1e. The ridges 6 are discontinuous, i.e. they form annular groups of ridges 6 in the longitudinal direction of the pin 1. The ridges 6 have alternating starting points. The ridges 6 may differ in length.

Figure 1G:
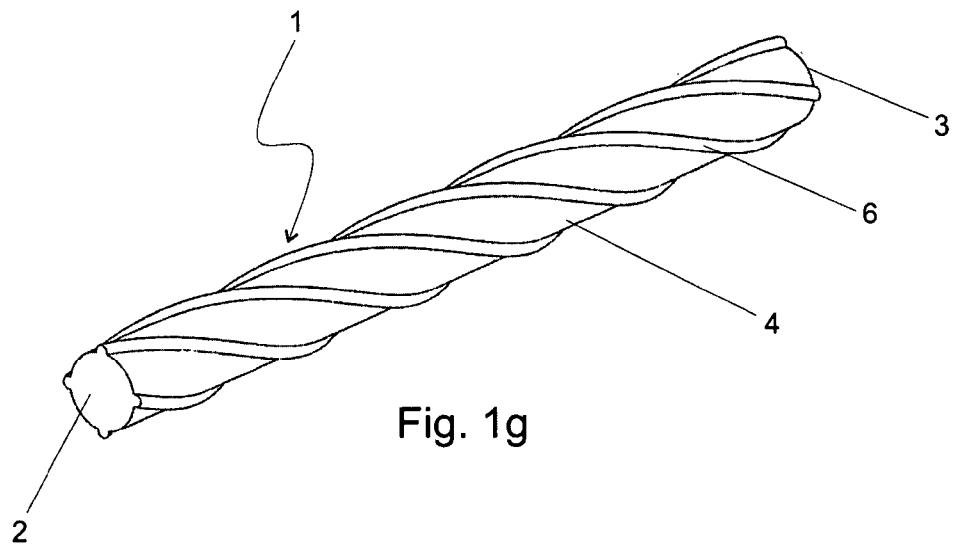

FIG. 1g shows a pin 1 whose ridges 6 extend spirally around the longitudinal axis of the pin 1.

Figure 1H:
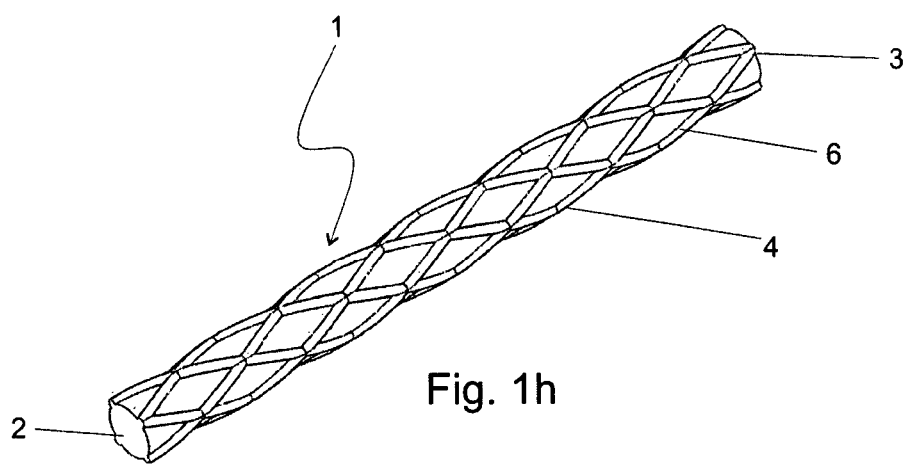

FIG. 1h shows a pin 1 whose ridges 6 extend spirally around the longitudinal axis of the pin 1 but half the ridges 6 have a different direction of rotation when compared to the other half. Thus, the ridges 6 cross each other.

Figure 1I:
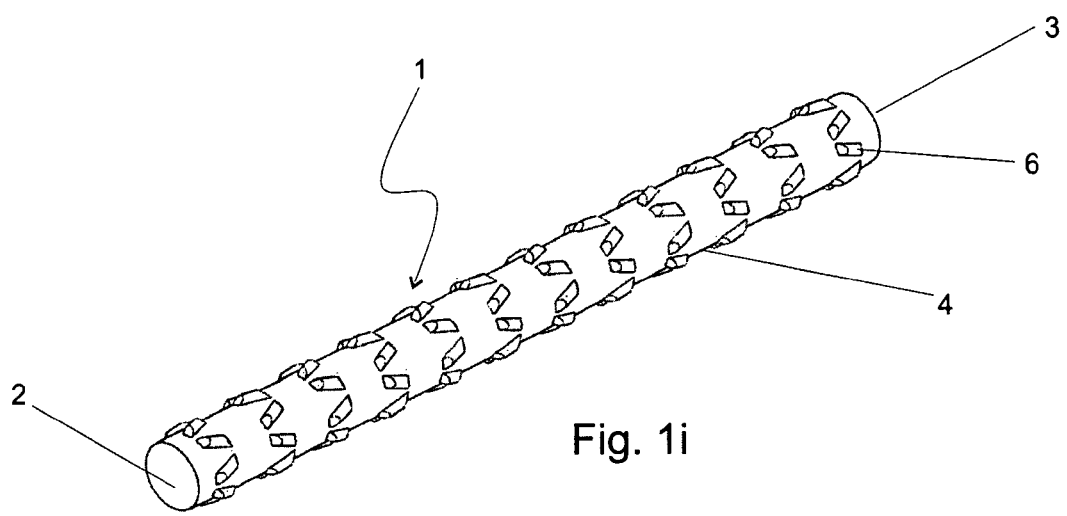

FIG. 1i shows a pin 1 whose ridges 6 extend spirally around the longitudinal axis of the pin, but the ridges 6 are discontinuous. Half the ridges 6 have a different direction of rotation when compared to the other half.

Figure 2:
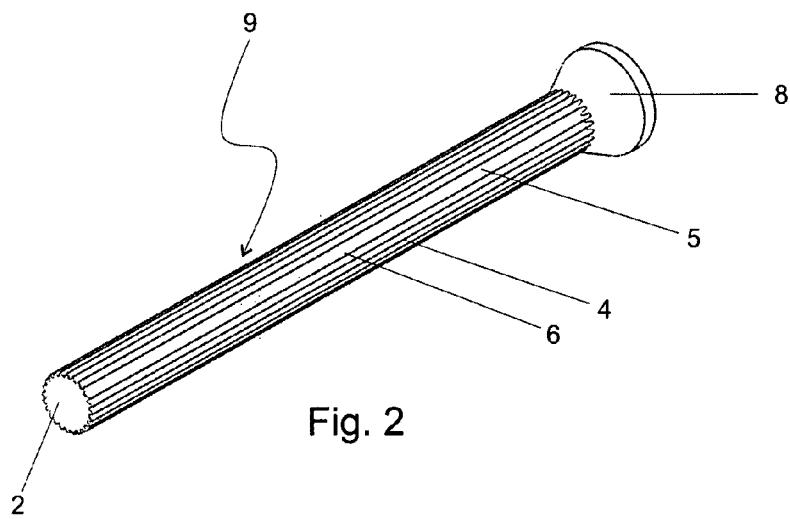
FIG. 2 shows a perspective view of a tack of the invention.

FIG. 2 shows a tack 9 of the invention. The head 8 of the tack 9 is wider than the shaft 4 of the tack 9. The head 8 may be a conical head.

Figure 3:
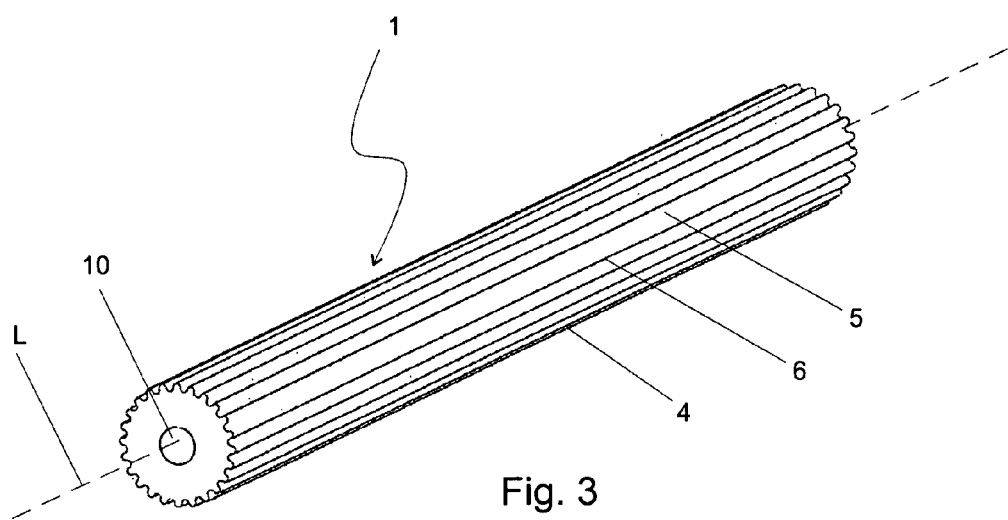
FIG. 3 shows a perspective view of a cannulated pin of the invention.

FIG. 3 shows a cannulated pin with a canal 10. The canal 10 extends through the pin along its longitudinal axis L.

Figure 4A:
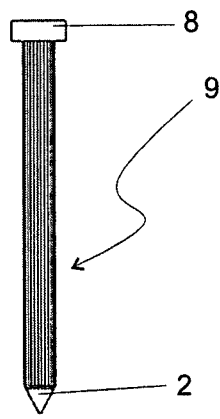
FIGS. 4a-4c show side views of tacks of the invention.
Figure 4B:
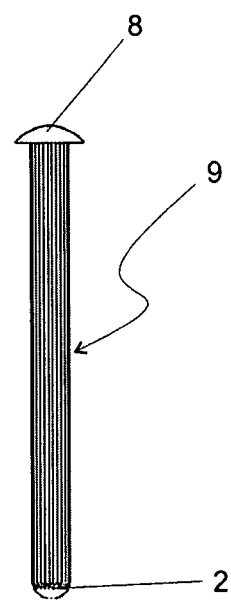
Figure 4C:
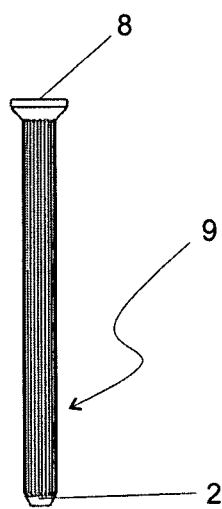

FIGS. 4a-4c show different shapes of the tack 9 of the invention. In FIG. 4a the head 8 is a flat circular plate and the tip 2 is a cone. In FIG. 4b the head 8 is convex and the tip is a sphere which is cut from its lowest point. In FIG. 4c the head 8 comprises a conical part and on top of the conical part a flat circular plate. The tip 2 is a truncated cone. The abovementioned shapes provide only a few examples of the possible variations. Naturally the shapes of the tips 2 are also useful in connection with the pin 1.

Figure 5A:
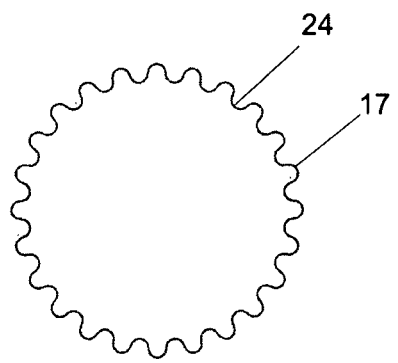
FIGS. 5a-5g show typical cross-sectional views of the geometries of the shafts of pins or tacks of the invention.
Figure 5B:
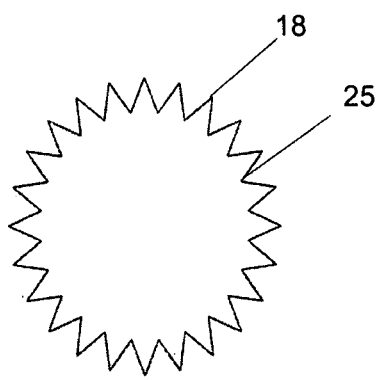
Figure 5C:
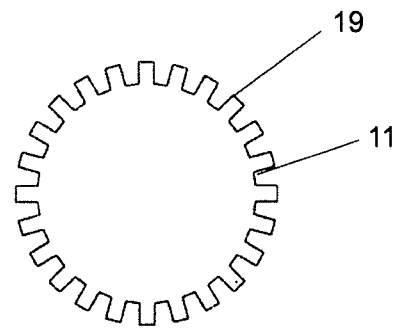
Figure 5D:
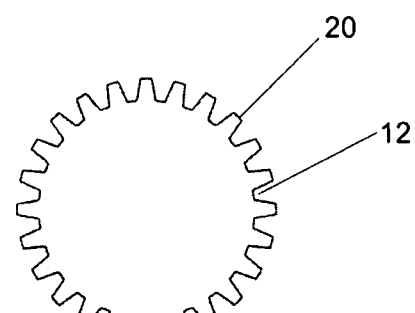
Figure 5E:
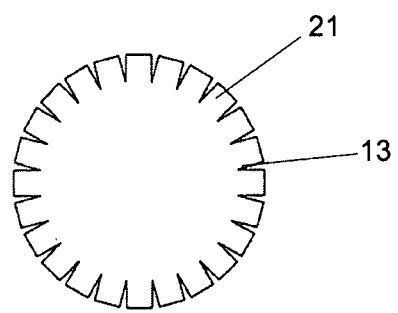
Figure 5F:
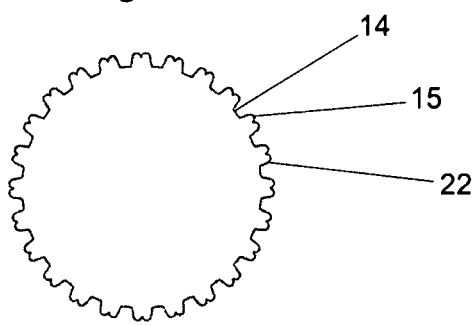
Figure 5G:
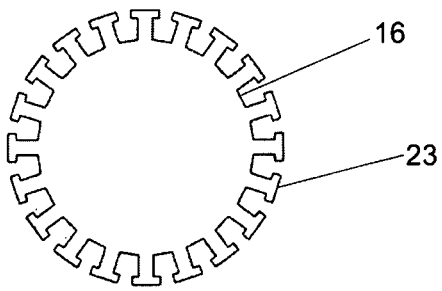

FIGS. 5a-5g show cross-sectional views (transverse to the longitudinal axis of a pin 1 or tack 9) of typical geometries of the grooves and ridges on the surface of the shaft 4 of the pin 1 or tack 9 of the invention. FIG. 5a shows a smooth, curved profile comprising grooves 24 and ridges 17. FIG. 5b shows sharp grooves 25 and ridges 18. FIG. 5c shows quadrangular grooves 11 and ridges 19. FIG. 5d shows grooves 12 and ridges 20 which taper towards the periphery of the shaft 4. FIG. 5e shows sharp grooves 13 and blunt, broad ridges 21. FIG. 5f shows broad grooves 14 and broad ridges 22 which additionally include smaller, narrow grooves 15. FIG. 5g shows broad grooves 16 and ridges 23 having a profile which resembles a mushroom. Naturally, other types of grooves and ridges and their combinations are also possible in order to attain the deformable surface structure to the shaft of a pin or tack of the invention. As one can see, all the cross-sections illustrated in FIGS. 5a-5g show alternating ridges and grooves which cover the whole circumference of the fixation device. When the ridges are evenly distributed over the whole circumference of the fixation device, each ridge causes only minor local stress towards the wall of the hole in which the fixation device has been inserted. Small canals are also formed between the wall of the hole and the outer circumference of the fixation device so that blood and tissue fluids can circulate in the canals, thus accelerating healing of the bone.

Figure 6:
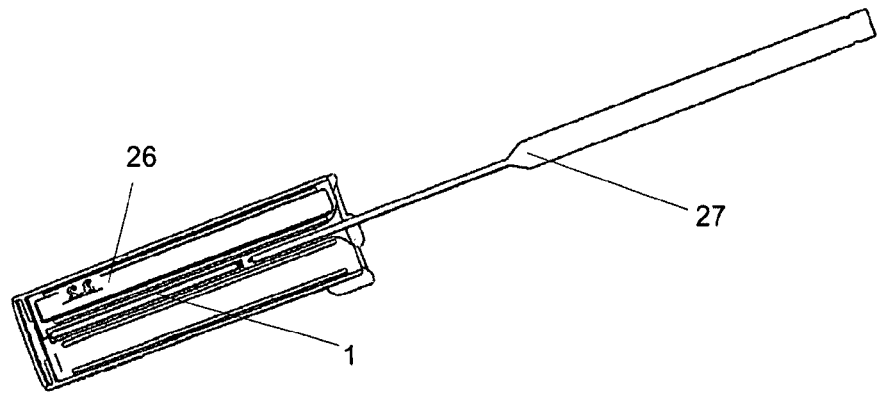
FIG. 6 shows a cross-sectional side view of a package comprising a fixation device and an innermost part of an applicator instrument.
Figure 7:
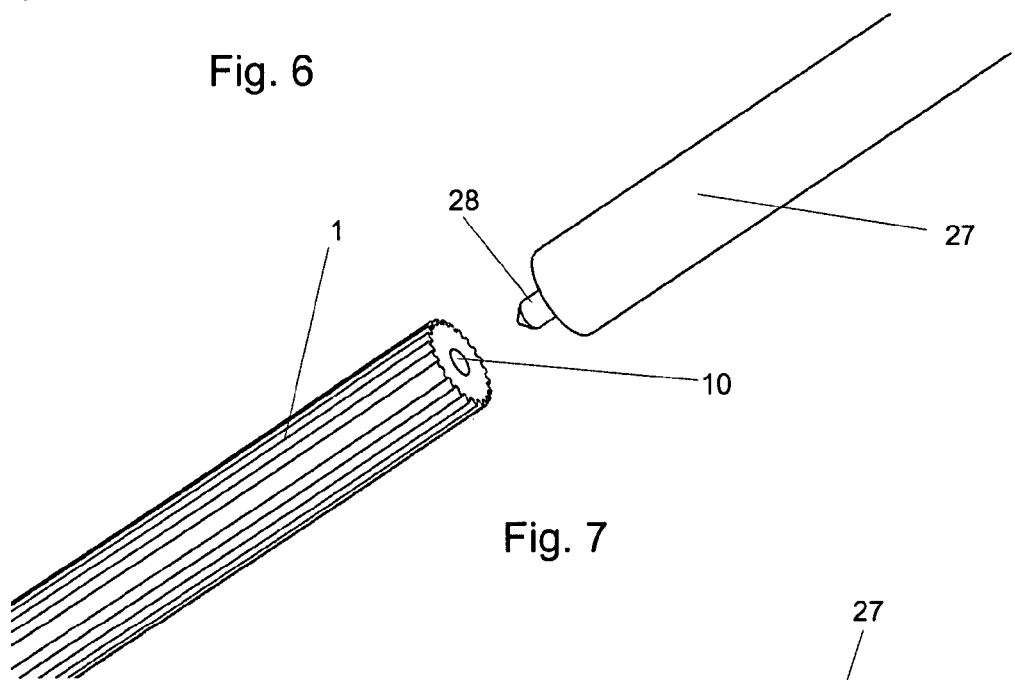
FIG. 7 shows a magnified perspective view of the fixation device and the innermost part of FIG. 6 (partial view)

In the following, the method for fixing a bone fracture is explained. At least one fixation device of the invention is used in the method. A fixation device, e.g. a pin 1, is stored in a special holder/package 26 as shown in FIG. 6. The fixation device comprises a cavity or a canal 10 which is concentric with the longitudinal axis of the device as shown in FIG. 7. The fixation device is picked from the holder 26 by pushing an innermost part 27 of a special applicator instrument into the holder 26 until the holder 26 meets the cavity or the canal 10 of the fixation device. The innermost part 27 comprises a tip 28 which is compatible with the cavity or the canal 10. The canal 10 extends through the fixation device but the cavity extends only so far that the tip 28 can penetrate into the cavity. The mounting between the fixation device and the instrument is achieved with a plug connection. The holder 26 supports and guides the fixation device and the instrument when the fixation device is picked by the instrument.

Figure 8:
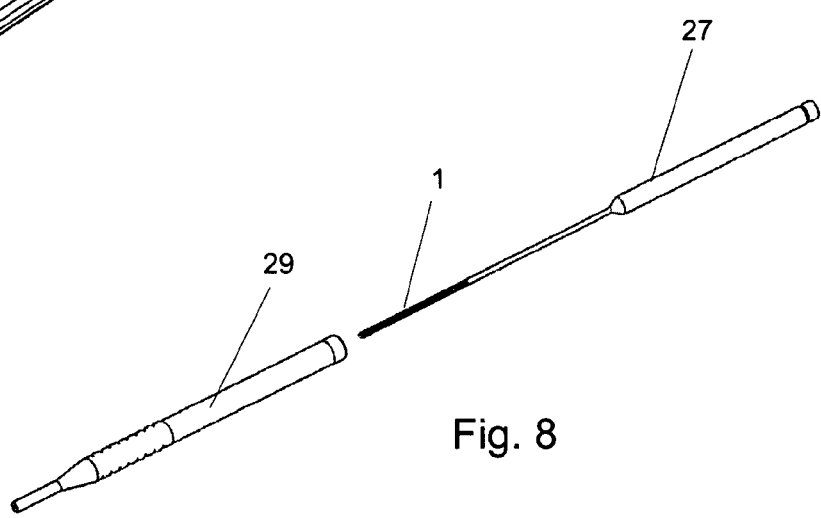
FIG. 8 shows a perspective view of the fixation device and the innermost part of FIGS. 6 and 7, and an outermost part.

The instrument comprises a special supporting part, i.e. an outermost part 29, into which the fixation device can be slid. After the fixation device is attached to the applicator instrument, the system can be rotated to the best fixation position or inside the innermost part 29 of the instrument before the insertion into a bone 31. As can be seen in FIG. 8, the fixation device is firmly attached to the instrument during the positioning and insertion by the plug connection. Due to the plug connection and the supporting and guiding holder/package 26, the fixation device can be picked on the instrument and inserted into the bone without touching the fixation device by hand, or dropping the fixation device, regardless of the insertion angle or the position of the instrument.

Figure 9:
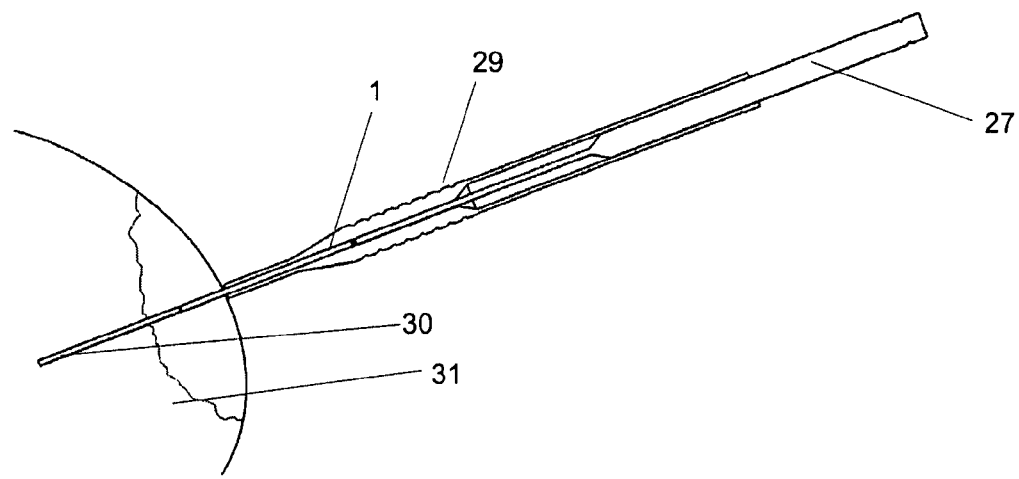
FIG. 9 shows a schematic cross-sectional view of an implanting process.

A hole 30 is drilled to the bone 31 for the fixation device as shown in FIG. 9. The diameter of the drill bit shall be selected according to the nominal diameter of the fixation device. The fixation device has a nominal diameter which determines unambiguously how large the diameter of the hole to be drilled in a bone must be, and that diameter is given in medical instructions which accompany the fixation device. However, when the drilled hole has an inaccurate diameter, e.g. due to an inaccurate drilling tool, the fixation device of the invention can still be inserted successfully to this hole. The fixation device has a capability to deform in two ways. When a bone in which a hole is drilled is substantially soft and brittle, the ridges of the fixation device penetrate in the wall of the hole. When a bone in which a hole is drilled is substantially hard and inflexible, the ridges are able to deform so that the diameter of the fixation device contracts, and it can be inserted in the hole.

Figure 16:
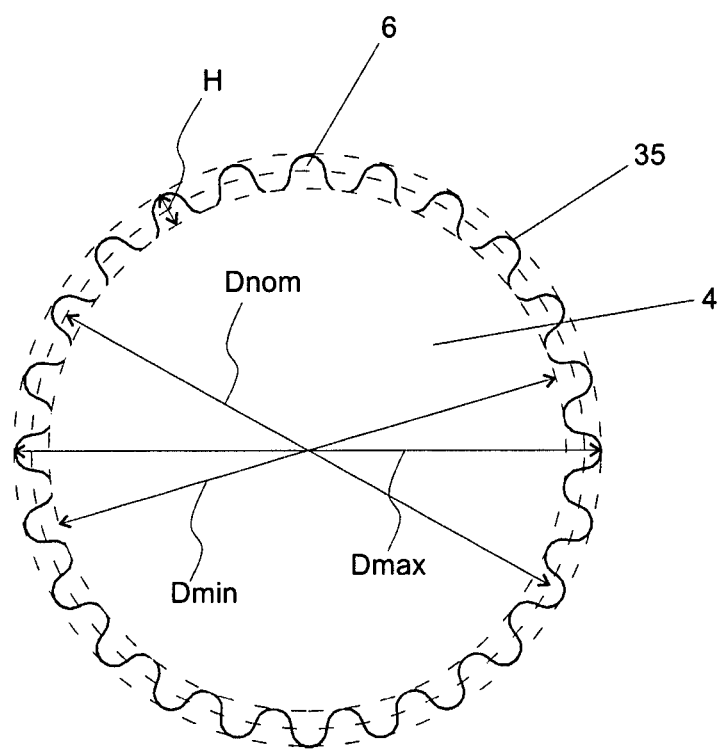

FIG. 16 shows a magnified view of the cross-section of FIG. 5a. Dmax is the maximum diameter of the shaft, extending from a top 35 of a ridge 6 through the centre of the shaft to an opposite top 35 of a ridge 6. Dmin is the minimum diameter of the shaft, i.e. the diameter of the solid shaft without the ridges 6. The nominal diameter Dnom may vary between Dmax and Dmin, i.e. the nominal diameter may vary within the height H of the ridge 6.

During the insertion of the fixation device, the applicator instrument and the fixation device are held in parallel to the longitudinal axis of the drillhole 30 so that the fixation device can slide safely into the drillhole 30. The fixation device is inserted by lightly tapping the instrument with a mallet until the entire fixation device is fully forced into the drillhole. The applicator instrument is designed so that it sinks the fixation device ca 0.5 or 1-2 mm below the bone (or cartilage) tissue surface when a piston is tapped to the end of the tube. This prevents the head of the fixation device from protruding which could cause soft tissue irritation.

After the insertion, if the pin is too long, scissors, a oscillating saw, or a hot wire can be used to cut the fixation device. In such a case, the proximal end of the pin must be pushed 1-2 mm below the cortical bone surface or smoothened at least to the cortical bone surface level, to avoid soft tissue irritation.

Two or more pin fixations can be applied, if necessary (depending on the nature and size of the fracture). In such a case the fixation devices, e.g. pins, are inserted at divergent angles to one another rather than in parallel, to obtain the best results.

On the basis of surgeon's decision, radiographs may be taken before wound closure.

After fixation, the wound is closed in layers applying standard principles of orthopaedics and traumatology. Meticulous hemostasis and complete primary skin closure over the implant are essential.

EXAMPLE

Tests Carried Out with the Fixation Device

Identification of the Test Samples

The test samples were pins manufactured by Bioretec Oy, said pins having a nominal diameter of 1.5 mm (LOT 051222 manufactured in December 2005 in the Bioretec production facility). The raw material of the pins was 85 L/15 G PLGA, with inherent viscosity of 5.5 dl/g (Boehringer Ingelheim GmbH, Germany), and the pins were gamma sterilized (Gamma-Service Produktbestrahlung GmbH, Germany). PLGA is a copolymer of L-lactide and glycolide, the amount of L-lactide was 85 wt.-% and the amount of glycolide was 15 wt.-%.

The pins were manufactured by melt extruding a longitudinal, cylindrical billet. The billet was uniaxially oriented in a die drawing process following the extruding process. In the die drawing process the billet was formed into its final grooved cross sectional shape. Between extruding and drawing there may be time for the billet to cool down, or the billet is actively cooled between these process steps. It is possible that the extruding process and the die drawing process take place on different process lines, or on the same process line, i.e. the process is a continuous process. Cutting, chamfering and drilling of an instrument hole, i.e. a cavity or a canal, in the pin was accomplished with mechanical machining. Manufacturing process phases and inspections were made according to Standard Operation Procedures (SOP) and technical drawings.

Identification of the Reference Samples

Pin products, which are currently marketed by a competitor, were used as reference samples. The nominal diameter of these pins was the same as the nominal diameter of the test samples. It should be noted that the reference samples represent the conventional fixation devices in which the nominal diameter is equal to the maximum diameter of the fixation device.

1. Biomechanical Pull-Out Test with Variable Drillholes
1.1. Objective of the Test The objective for the test was to study the insertion feel and compare the influence of different drill bit diameters on the biomechanical pull-out forces. This test was executed to evaluate and prove the adaptability of the pins into inaccurate drillholes caused by inaccurate drill bit diameter or multiple reaming. A pin according the present invention having a nominal diameter of 1.5 mm and a commercial reference sample having a nominal diameter of 1.5 mm were used in the test. The reference sample had a smooth surface. The used pull-out test method was modified from the standard ASTM F 2502-05.

1.2. Test Methods and Procedures

The test was carried out using a standard tensile testing machine (Lloyd 2000S, Fareham, UK). Pins were inserted into the distal end of a porcine cadaver femur. Three parallel samples of both pins were inserted 20 mm deep into drillholes made with 1.40, 1.45, 1.50, 1.55 and 1.6 mm drill bits.

The pins were installed randomly in the varying locations in the epiphysis. The test was carried out at room temperature (23° C.±4° C.). The bone was stored in a refrigerator and tested after slow melting and tempering. The pins were inserted using corresponding insertion instruments. Only one bone was used in order to minimize the variations in results caused by the difference in the bone quality.

1.3. Calculations

The maximum pullout force was measured in Newtons. No calculations have been performed to manipulate the data.

1.4. Results for Biomechanical Pull-Out Tests with Variable Drillholes

The average maximum pull-out forces from different drillhole sizes are represented in the table below.

TABLE 1

The maximum biomechanical pull-out force measurement results for the pin of the invention and the commercial reference sample. and the adaptability with different drillhole sizes in porcine cadaver femur (I = the pin of the invention. R = the reference sample).

| Sample | 1.40 drill bit | | 1.45 drill bit | | 1.50 drill bit | | 1.55 drill bit | | 1.60 drill bit | |
|---|---|---|---|---|---|---|---|---|---|---|
| | R | I | R | I | R | I | R | I | R | I |
| 1 | 20.56 | 77.10 | 24.41 | 145.00 | 8.05 | 32.31 | 3.74 | 4.54 | — | 10.53 |
| 2 | 95.10 | 155.90 | 22.93 | 104.80 | 14.61 | 95.63 | 0.50 | 32.35 | — | 13.35 |
| 3 | 18.16 | 185.80 | 18.84 | 124.70 | 3.40 | 185.00 | 1.37 | 20.98 | — | 12.97 |
| Average | 44.61 | 139.60 | 22.06 | 124.83 | 8.68 | 104.31 | 1.87 | 19.29 | — | 12.28 |
| Min | 18.16 | 77.10 | 18.84 | 104.80 | 3.40 | 32.31 | 0.50 | 4.54 | — | 10.53 |
| Max | 95.10 | 185.80 | 24.41 | 145.00 | 14.61 | 185.00 | 3.74 | 32.35 | — | 13.35 |

Figure 11:
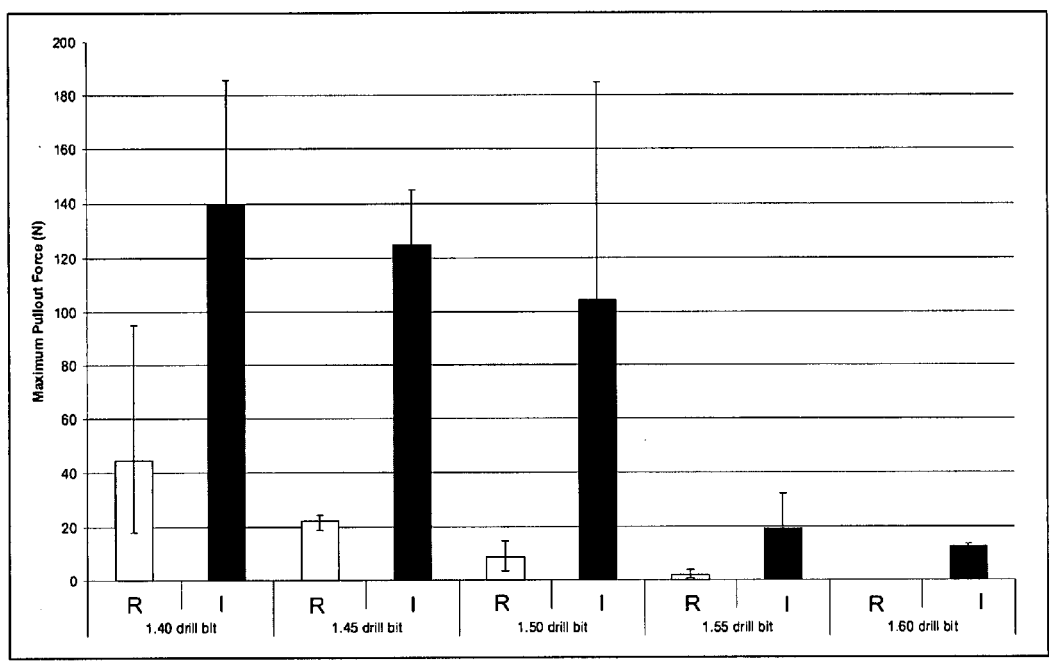
FIG. 11 shows a graphical representation of maximum biomechanical pull-out forces from different drillhole sizes in porcine cadaver femur for the pin of the invention and the reference sample.

The reference sample 2 pulled from the 1.4 mm hole broke during pullout. All the remaining pins were successfully pulled out from the bone. The measurements could not be carried out for the reference samples from the 1.6 mm drillhole, because the force levels were too low to be measured in this test setup. Such low forces are also most likely clinically negligible. FIG. 11 shows the data graphically. The error bars in the graph represent the measured minimum and maximum values.

The installation feel was good for the pin of the invention into the 1.40 to 1.55 mm drillholes, but somewhat loose into the 1.60 mm drillhole. The reference sample was difficult to install into holes smaller than 1.45 mm because of too tight an insertion feel. The insertion feel was too loose into holes bigger than 1.50 mm for the reference sample.

1.5. Conclusions for Biomechanical Pull-Out Tests with Variable Drillholes

The biomechanical average maximum pull-out force of the pin of the invention having the nominal diameter of 1.5 mm was at least three times higher than that of the reference sample having the same nominal diameter. The test results demonstrate that the surface design of the pin of the invention reduces the risk of unstable fixation and gives more tolerance for instrumentation, bone quality and surgical procedure.

2. Biomechanical Rotation Stability Test

The objective of the test was to evaluate the rotation stability of the pins inserted into the bone tissue. Comparison was made between the pin of the invention having a nominal diameter of 1.5 mm and the reference commercial sample having the same nominal diameter. Used rotation stability test method was modified from the standard ASTM F 2502-05.

2.1. Materials and Methods

Figure 10:
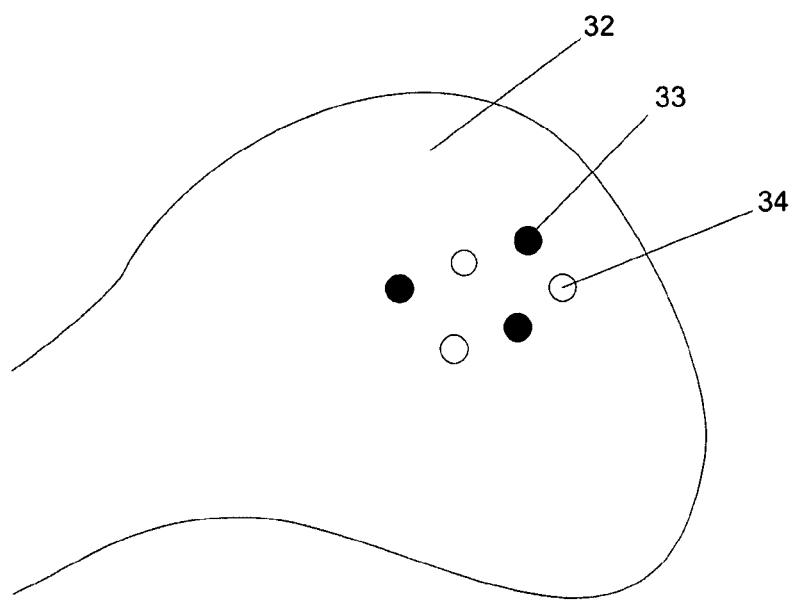
FIG. 10 shows a schematic view of an end of a porcine femur.

The test was carried out using a standard tensile testing machine (Instron 4411) equipped with a rotation unit. Pins were inserted into the lateral side of the distal end of a porcine cadaver femur. Three parallel samples of both pins were inserted 20 mm deep into drillholes made with a 1.5 mm drill bit. The locations of the drillholes are shown in FIG. 10.

The pins of the invention were installed one pin at a time in the locations marked with black circles 33 and the reference samples in the locations marked with white circles 34. The test was carried out in room temperature (23° C.±4° C.). The bone 32 was stored in a refrigerator and tested after slow melting and tempering. Pins were inserted using corresponding insertion instruments. The rotation speed was 0.76 rpm during testing.

2.2. Calculations

The resistance of rotation was measured in Newtons from the linearly moving load cell as a function of linear movement. The values were calculated to torque as a function of rotation angle using equations represented below.

Measured Load to Torque:

$$T = F \times r, \text{ wherein}$$

Figure 12:
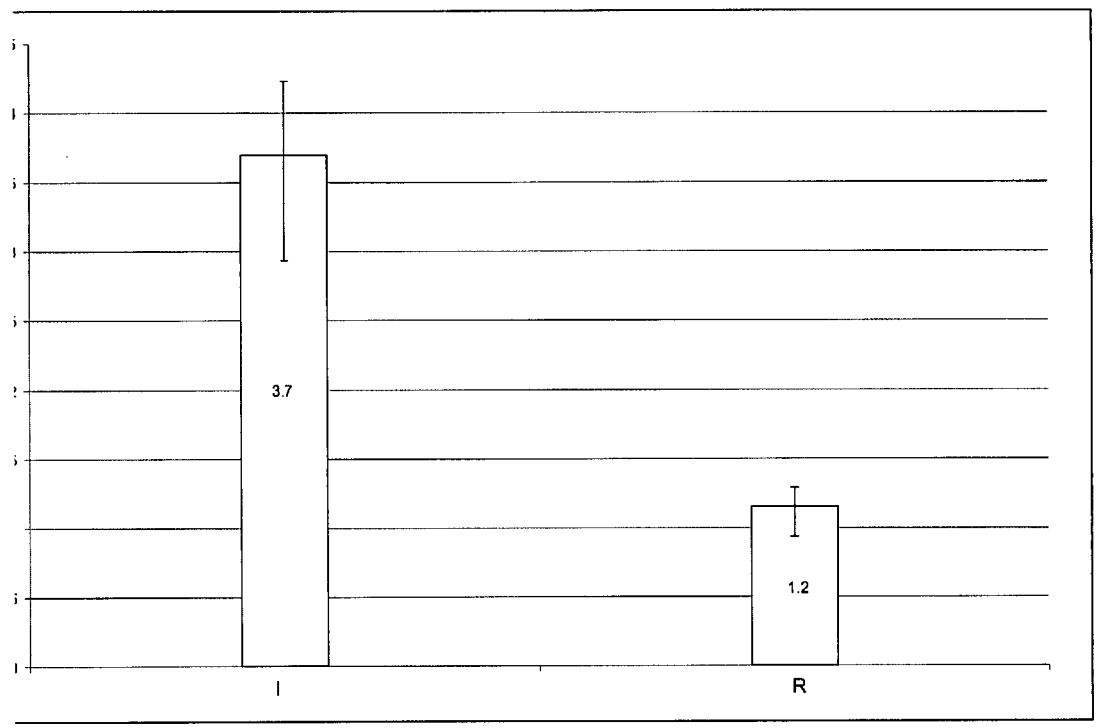
FIG. 12 shows a graphical representation of maximum torque values within first 90° of rotation of the pin of the invention having the nominal diameter of 1.5 mm and the reference sample having the same nominal diameter.

T=Torque [Ncm]
F=Force [N]=Measured load from the linearly moving load cell
r=Radius of the wheel of the measurement apparatus [cm]= 4.375 cm Measured Linear Motion to Angle:

$$\alpha = (360° \times h)/(2 \times \pi \times r), \text{ wherein}$$

α=Angle of rotation [°]
h=Linear movement distance [cm]
r=Radius of the wheel of the measurement apparatus [cm]= 4.375 cm 2.3. Results for Biomechanical Rotation Stability Test The average maximum torque values of first 90° of rotation measured for the pin of the invention having the nominal diameter of 1.5 mm and the reference sample having the same nominal diameter were 3.7 (min 2.9 max 4.2) Ncm and 1.2 (min 0.9 max 1.3) Ncm, respectively. FIG. 12 shows the measurement results graphically. The error bars in the graph represent the measured minimum and maximum values.

Figure 13:
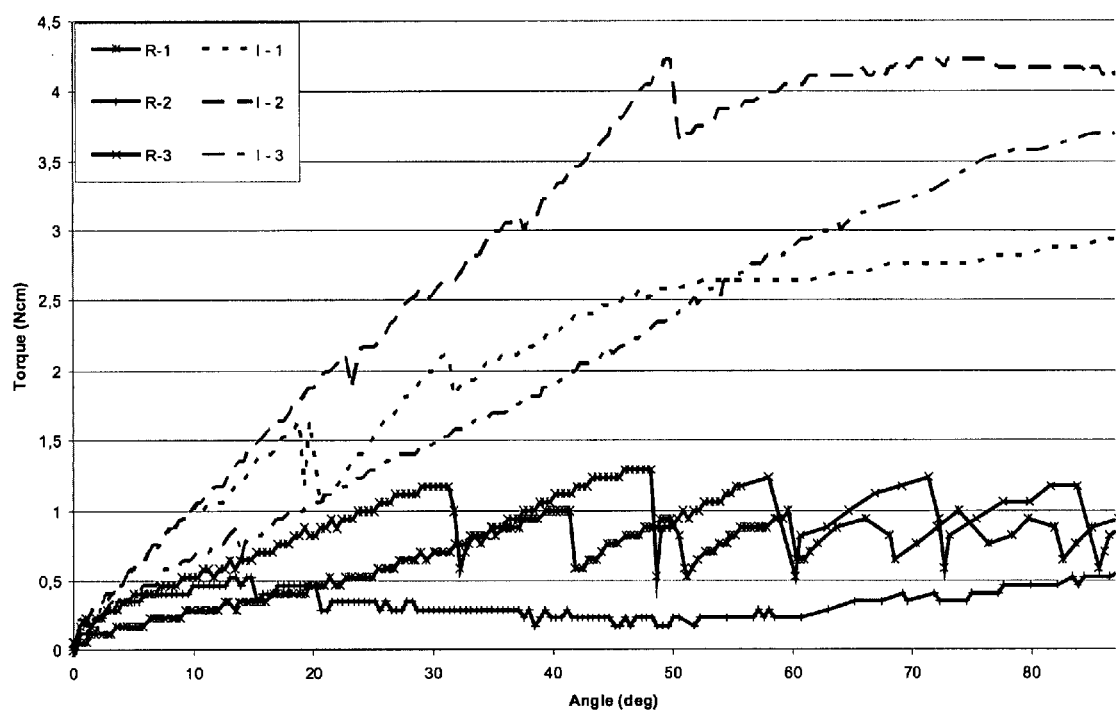
FIG. 13 shows a graphical representation of measured torque as a function of a rotation angle up to 90° for all the 6 tested samples.

FIG. 13 represents graphically the measured data of all the 6 samples up to the rotation angle of 90°.

Figure 14:
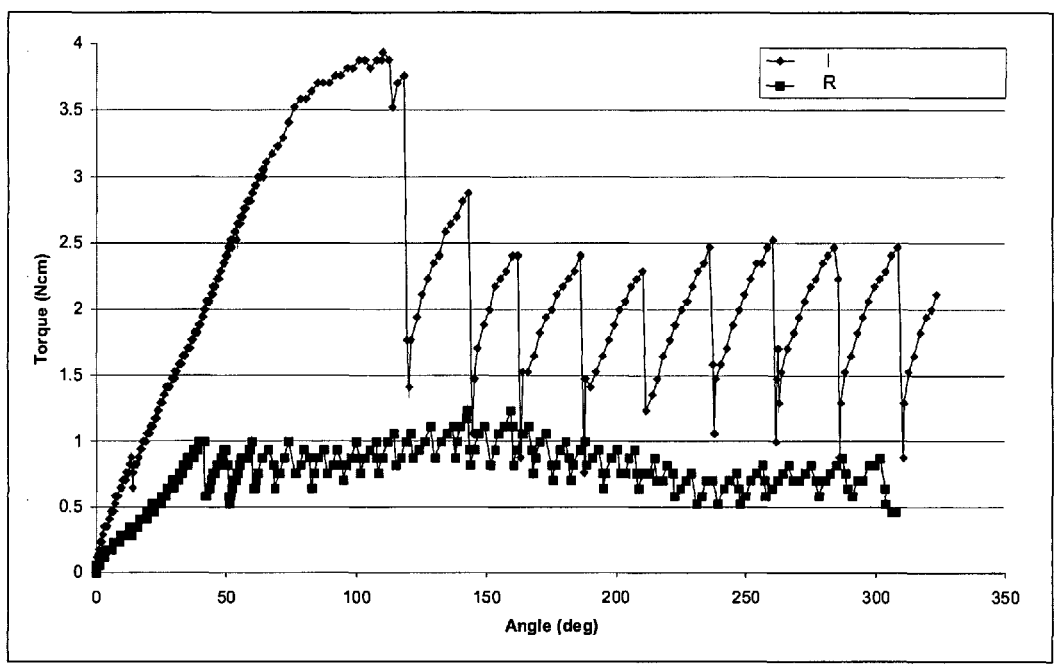
FIG. 14 shows an example of typical rotation stability graphs of the pin of the invention and the reference sample.

The three uppermost curves represent the three parallel samples of the pin of the invention having the nominal diameter of 1.5 mm and the three lower curves represent the three parallel samples of the reference sample having the same nominal diameter. The failure mode of the fixation in case of the pins of the invention was the rotation of the pin in the hole in two cases and the twisting of the pin in one case. The failure mode of fixation in case of the reference samples was the rotation of pin in the hole in all cases. FIG. 14 highlights the differences in the rotation stability of the pin of the invention and the reference sample.

The torque level a pin must overcome to start rotating in the hole is much higher in the case of the pin of the invention than in the case of the reference sample. Additionally, the graph reveals the effect of longitudinal grooves on the pin surface, when the pin is further rotated in the bone after the initially required torque level is exceeded.

2.4. Conclusions for Biomechanical Rotation Stability Test

The grooved surface design improves the rotation stability of the pin of the invention significantly when compared to the reference samples with round and plain pin surface. The tested rotation stability values for the pin of the invention were two to three times higher than the values for the reference sample.

3. Biomechanical In Vitro Pull-Out Test for the Pin of the Invention 3.1. Objective of the Test The objective of this test was to study and determine the hydrolytic self-locking effect of the oriented pin of the invention. This feature is caused by dimensional changes of the pin during hydrolysis.

3.2. Test Articles

Pin samples of 1.5 mm×40 mm were used in the test.

3.3. Test Methods and Procedures

Tests were performed using cadaver porcine bones. Pins were inserted into the bone in accordance with normal surgical procedures. In vitro hydrolysis test at +37° C. in Sörensen Buffer, pH 7.4±0.2 was carried out for the bones containing the inserted pins.

Biomechanical pull-out properties were tested at 0, 4, 8, 23 and 63 hours. Three parallel samples per each point of time were tested.

The test was performed with wet samples in room temperature (23° C.±4° C.), and the maximum pull-out forces were recorded in Newtons during the test. Pull-out force was applied to the test specimen at a rate of 10 mm/min.

3.4. Results for Biomechanical In Vitro Pull-Out Tests

Figure 15:
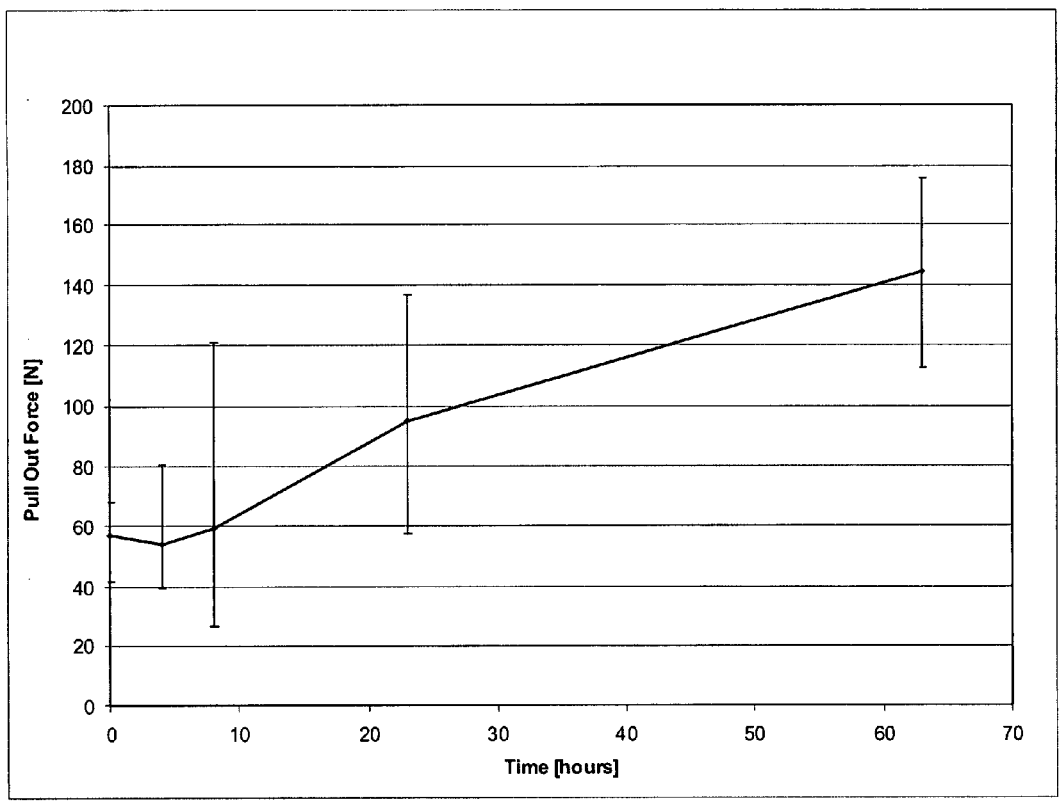
FIG. 15 shows biomechanical in vitro pull-out test results of the pin of the invention having a nominal diameter of 1.5 mm.

The mechanical feature of the oriented pins of the invention which causes the hydrolytic self-locking effect could be seen during the biomechanical in vitro pull-out tests. The required pull-out force gradually increased during the 63 hour test time. Results are presented with numeric values in Table 2 and in graph form in FIG. 15.

TABLE 2

Pull-out test results for the 1.5 × 40 mm pin of the invention.

| | TIMEPOINT | | | | |
|---|---|---|---|---|---|
| | 0 hours | 4 hours | 8 hours | 23 hours | 63 hours |
| Sample 1 | 61.45 N | 42.69 N | 30.14 N | 137.1 N | 145 N |
| Sample 2 | 68.28 N | 80.45 N | 120.9 N | 91.06 N | 112.3 N |
| Sample 3 | 41.43 N | 39.52 N | 26.74 N | 57.68 N | 175.8 N |
| Average | 57.05 N | 54.22 N | 59.26 N | 95.28 N | 144.37 N |

3.5. Conclusions for Biomechanical In Vitro Pull-Out Tests

The maximum pull-out force gradually increases during the 63 hour test time. This is a consequence of the hydrolytic locking effect for the pin. This behavior is outcome of the dimensional changes of the oriented pin of the invention during the hydrolysis.

4. Conclusions for Biomechanical Testing

Biomechanical testing demonstrated that this new surface design of the pin surprisingly offers advantage in relation to the biomechanical properties, and that it creates the desired advantage into the biomechanical properties of the pin, when compared to previously legally marketed devices used for the same purposes.

The biomechanical pull-out test determined that the grooved surface design of the pin causes improved instant self-locking effect into a drillhole when compared to the reference sample device. The tested pull-out forces after implantation were ca 10 times higher for the 1.5 mm pin of the invention than those of the reference sample device.

The biomechanical pull-out tests with variable drillholes determined that the average maximum pull-out force of the 1.5 mm pin of the invention was typically two to three times higher than that of the reference sample having the same diameter. The test results demonstrate that the surface design of the pin of the invention reduces the risk of unstable fixation and gives more tolerance for instrumentation, bone quality and surgical procedure than the reference sample.

The biomechanical rotation stability tests determined that the grooved surface design improves rotation stability of the pin of the invention when compared to the reference samples with a round and plain pin surface (cylindrical pin geometry). The tested rotation stability values for the pin of the invention were ca three times higher than the values for the reference sample.

Biomechanical in vitro pull-out tests determined that the maximum pull-out force of pins of the invention gradually increases during the 63 hour test time. This is a consequence of the hydrolytic self-locking effect for the pin. This behavior is an outcome of the dimensional changes of the pin of the invention during the hydrolysis.

The same dimensional change could be seen during the in vitro hydrolysis test series of the pin of the invention which were ongoing at the same time with the in vitro pull-out tests. During this test the pin of the invention gradually changed its dimensions. After 2 weeks of hydrolysis, the diameter of the pin was increased 0.5%-1% and its length was decreased 0.5%-1% when compared to the initial dimensions. After 6 weeks of hydrolysis, the diameter of the pin was increased 1%-2% and its length was decreased 1%-2% when compared to the initial dimensions. These dimensional changes are sufficient to create hydrolytic self-locking, but small enough not to adversely affect the safety or effectiveness of the fixation with the pin of the invention.

As one skilled in the art can readily understand, one can easily produce various modifications of the above-described fixation device which also naturally belong to the scope of the claims.

The invention claimed is:

1. A bioabsorbable osteosynthesis fixation device for fixation of bone fractures or osteotomies, the fixation device comprising:
    a tip,
    a head, and
    a shaft having a longitudinal axis, a nominal diameter corresponding to a diameter of a hole in which the device is inserted, a minimum diameter and a maximum diameter, a periphery of the shaft comprising ridges extending from the minimum diameter of the shaft to the maximum diameter of the shaft, wherein the ridges extend in a longitudinal direction of the shaft which forms an angle with the longitudinal axis of the shaft, the angle being between $-45°$ and $45°$, wherein the nominal diameter of the shaft is less than the maximum diameter and greater than the minimum diameter, and wherein the fixation device is molecularily oriented having a drawing ratio of between 2 and 5 in a longitudinal direction of the device, wherein a diameter of a hole in which the device is inserted depends upon the nominal diameter, and wherein the ridges are configured to deform in bone that is harder than the ridges and penetrate bone that is softer than the ridges.

2. The bioabsorbable osteosynthesis fixation device according to claim 1, wherein the angle formed with the longitudinal axis is between $-10°$ and $10°$.

3. The bioabsorbable osteosynthesis fixation device according to claim 1, wherein the angle formed with the longitudinal axis is between $-5°$ and $5°$.

4. The bioabsorbable osteosynthesis fixation device according to claim 1, wherein the ridges extend in a direction which is parallel to the longitudinal axis.

5. The bioabsorbable osteosynthesis fixation device according to claim 1, wherein the ridges form a spiral around the longitudinal axis.

6. The bioabsorbable osteosynthesis fixation device according to claim 1, wherein the ridges are discontinuous.

7. The bioabsorbable osteosynthesis fixation device according to claim 1, wherein the fixation device is a pin or a tack.

8. The bioabsorbable osteosynthesis fixation device according to claim 1, wherein the diameter of the fixation device increases within the first 63 hours in a test in vitro, thus increasing a pull-out force of the fixation device.

9. The bioabsorbable osteosynthesis fixation device according to claim 1, wherein the fixation device comprises a copolymer of L-lactide and glycolide.

10. The bioabsorbable osteosynthesis fixation device according to claim 1, wherein the nominal diameter corresponds to a diameter of a hole in which the device is inserted.

11. A bioabsorbable osteosynthesis fixation device, comprising:
    a conical tip,
    a head,
    a shaft having a longitudinal axis, a nominal diameter, a minimum and a maximum diameter, a periphery of the shaft comprising over a whole circumference of the shaft alternating grooves and ridges extending from the minimum diameter of the shaft, wherein the grooves and ridges extend in a longitudinal direction of the shaft which is parallel to the longitudinal axis, wherein the nominal diameter of the shaft is less than the maximum diameter and greater than the minimum diameter, and wherein the fixation device is molecularily oriented having a drawing ratio of between 2 and 5 in a longitudinal direction of the device, wherein a diameter of a hole in which the device is inserted depends upon the nominal diameter, and wherein the ridges are configured to deform in bone that is harder than the ridges and penetrate bone that is softer than the ridges, and
    a cavity which is concentric with the longitudinal axis of the fixation device.

12. The bioabsorbable osteosynthesis fixation device according to claim 11, wherein the ridges are discontinuous.

13. The bioabsorbable osteosynthesis fixation device according to claim 11, wherein the fixation device is a pin or a tack.

14. The bioabsorbable osteosynthesis fixation device according to claim 11, wherein the diameter of the fixation device increases within the first 63 hours in a test in vitro, thus increasing a pull-out force of the fixation device.

15. The bioabsorbable osteosynthesis fixation device according to claim 11, wherein the fixation device comprises a copolymer of L-lactide and glycolide.

16. The bioabsorbable osteosynthesis fixation device according to claim 11, wherein the nominal diameter corresponds to a diameter of a hole in which the device is inserted.

17. A bioabsorbable osteosynthesis fixation device for fixation of bone fractures or osteotomies, the fixation device comprising:
    a tip,
    a head, and
    a shaft having a longitudinal axis, a nominal diameter, a minimum diameter and a maximum diameter, a periphery of the shaft comprising ridges extending from the minimum diameter of the shaft, wherein the ridges extend in a longitudinal direction of the shaft which forms an angle with the longitudinal axis of the shaft, the angle being between $-5°$ and $5°$, wherein the nominal diameter of the shaft is less than the maximum diameter and greater than the minimum diameter, and wherein the fixation device is molecularily oriented having a drawing ratio of between 2 and 5 in a longitudinal direction of the device, wherein a diameter of a hole in which the device is inserted depends upon the nominal diameter, and wherein the ridges are configured to deform in bone that is harder than the ridges and penetrate bone that is softer than the ridges.

18. The bioabsorbable osteosynthesis fixation device according to claim 17, wherein the ridges are discontinuous.

19. The bioabsorbable osteosynthesis fixation device according to claim 17, wherein the fixation device is a pin or a tack.

20. The bioabsorbable osteosynthesis fixation device according to claim 17, wherein the diameter of the fixation device increases within at least the first six weeks, in a test in vitro, thus increasing a pull-out force of the fixation device.

21. The bioabsorbable osteosynthesis fixation device according to claim 17, wherein the fixation device comprises a copolymer of L-lactide and glycolide.

22. The bioabsorbable osteosynthesis fixation device according to claim 17, wherein the diameter of the fixation device increases within a first 63 hours in a test in vitro, thus increasing a pull-out force of the fixation device.

23. The bioabsorbable osteosynthesis fixation device according to claim 17, wherein the nominal diameter corresponds to a diameter of a hole in which the device is inserted.

* * * * *